(12) United States Patent
Dudley et al.

(10) Patent No.: US 8,715,646 B2
(45) Date of Patent: May 6, 2014

(54) METHODS OF DETERMINING NEED FOR ANTI-COAGULATION THERAPY

(75) Inventors: Samuel Dudley, Chicago, IL (US); Smita Negi, Houston, TX (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/812,639

(22) PCT Filed: Jul. 29, 2011

(86) PCT No.: PCT/US2011/045903
§ 371 (c)(1),
(2), (4) Date: Apr. 12, 2013

(87) PCT Pub. No.: WO2012/016150
PCT Pub. Date: Feb. 2, 2012

(65) Prior Publication Data
US 2013/0209435 A1   Aug. 15, 2013

Related U.S. Application Data

(60) Provisional application No. 61/368,941, filed on Jul. 29, 2010.

(51) Int. Cl.
*C12Q 1/56* (2006.01)
*G01N 33/86* (2006.01)

(52) U.S. Cl.
USPC ................................. 424/94.5; 435/13

(58) Field of Classification Search
USPC ................................. 424/94.5; 435/13
See application file for complete search history.

(56) References Cited

U.S. PATENT DOCUMENTS

| | | | |
|---|---|---|---|
| 6,355,489 B1 | 3/2002 | Carratelli | |
| 7,550,299 B2 * | 6/2009 | Dudley et al. | 436/86 |
| 2007/0218457 A1 | 9/2007 | McKim | |
| 2008/0033258 A1 * | 2/2008 | Dudley et al. | 600/300 |
| 2009/0325163 A1 * | 12/2009 | Helgadottir et al. | 435/6 |
| 2010/0233727 A1 | 9/2010 | Dudley, Jr. et al. | |

OTHER PUBLICATIONS

Altamura et al., Ceruloplasmin/transferrin system is related to clinical status in acute stroke, Stroke, 40:1282-8 (2009).
Berliner et al., Unique in vivo applications of spin traps, Free Radic. Biol. Med., 30(5):489-99 (2001).
CHADS2 score, Wikipedia entry, downloaded from the Internet: <http://en.wikipedia.org/wiki/CHADS2_score> (page last modified on Sep. 20, 2013).
Chung et al., C-reactive protein elevation in patients with atrial arrhythmias: inflammatory mechanisms and persistence of atrial fibrillation, Circulation 104(24):2886-91 (2001).
Cohen et al., Randomized, double-blind, dose-ranging study of otamixaban, a novel, parenteral, short-acting direct factor Xa inhibitor, in percutaneous coronary intervention: the SEPIA-PCI trial, Circulation, 115(20):2642-51 (2007).
Conway et al., Predictive value of indexes of inflammation and hypercoagulability on success of cardioversion of persistent atrial fibrillation, Am. J. Cardiol., 94(4):508-10 (2004).
Cornelli et al., Bioavailability and antioxidant activity of some food supplements in men and women using the D-Roms test as a marker of oxidative stress, J. Nutr., 131(12):3208-11 (2001).
Crandall et al., Atrial fibrillation and CHADS2 risk factors are associated with highly sensitive C-reactive protein incrementally and independently, Pacing Clin. Electrophysiol., 32(5):648-52 (2009).
d-ROMs Test, Diacron International, downloaded from the Internet at: <http://www.diacron.com/en/carratelli-panel/droms.html> (accessed Oct. 2, 2013).
DeFranceschi et al., "Oxidative stress in coronary surgery", abstract only, Proceedings 6th international symposium on global risk of coronary heart disease and stroke: assessment, prevention, and treatment. Jun. 12-15, 2002, Florence Italy.
DeFranceschi et al., "Antioxidant capacity in coronary artery disease", abstract only, Proceedings 6th international symposium on global risk of coronary heart disease and stroke: assessment, prevention, and treatment. Jun. 12-15, 2002, Florence Italy.
Diacron International 2013 Catalogue, Panel Carratelli for Oxidative Stress Assessment (2013).
Eriksson et al., A once-daily, oral, direct Factor Xa inhibitor, rivaroxaban (BAY 59/7939), for thromboprophylaxis after total hip replacement Circulation, 11422):2374-81 (2006).
Gage et al., Validation of clinical classification schemes for predicting stroke: results from the National Registry of Atrial Fibrillation, JAMA, 285(22):2864-70 (2001).
Halliwell et al., Measuring reactive species and oxidative damage in vivo and in cell culture: how should you do it and what do the results mean? Br. J. Pharmacol., 142(2):231-55 (2004).
Huo et al., Dexamethasone inhibits the Nox-dependent ROS production via suppression of MKP-1-dependent MAPK pathways in activated microglia, BMC Neurosci., 12:49 (2011).
International Preliminary Report on Patentability for international application No. PCT/US11/45903, dated Apr. 9, 2013.
International Search Report and Written Opinion for international application No. PCT/US11/45903, mailing date Apr. 9, 2012.
Iwatsuki et al., Experimental model of lower limb ischemia in rats and the effect of YM466, an oral direct factor Xa inhibitor, Biol. Pharm. Bull., 30(10):1874-7 (2007).
Kamezaki et al., Derivatives of reactive oxygen metabolites correlates with high-sensitivity C-reactive protein, J. Artherosclerosis Thrombosis, 15(4):206-12 (2008).
Kanaoka et al., Analysis of reactive oxygen metabolites (ROMs) after cardiovascular surgery as a marker of oxidative stress, Acta. Med. Okayama, 64(5):223-30 (2010).
Long et al., Hydrogen peroxide in human urine: implications for antioxidant defense and redox regulation, Biochem. Biophys. Res. Commun., 262(3):605-9 (1999).
Maeda et al., Clinical evaluation of oxidative stress and antioxidant potentials in stroke patients, European Stroke Conference, Poster Abstract No. 957 (2010).

(Continued)

*Primary Examiner* — Ralph Gitomer
(74) *Attorney, Agent, or Firm* — Marshall, Gerstein & Borun LLP

(57) ABSTRACT

Provided herein are methods of determining a subject's need for anti-coagulation therapy. In exemplary embodiments, the method comprises measuring a level of derivatives of reactive oxygen metabolites (DROMs) in a biological sample obtained from the subject. In exemplary embodiments, the method comprises measuring a level of C-reactive protein (hs-CRP).

6 Claims, 2 Drawing Sheets

(56) References Cited

OTHER PUBLICATIONS

Neuman et al., Oxidative stress markers are associated with persistent atrial fibrillation, Clin. Chem., 53(9):1652-7 (2007).

Paccaly et al., Pharmacodynamic markers in the early clinical assessment of otamixaban, a direct factor Xa inhibitor, Thromb. Haemost., 94(6):1156-63 (2005).

Pamukcu et al., Simplifying stroke risk stratification in atrial fibrillation patients: implications of the CHA2DS2-VASc risk stratification scores, Age Ageing, 39(5):533-5 (2010).

Puwanant et al., Role of the CHADS2 score in the evaluation of thromboembolic risk in patients with atrial fibrillation undergoing transesophageal echocardiography before pulmonary vein isolation, J. Am. Coll. Cardiol., 54(22):2032-9 (2009).

Reid et al., In vivo rates of erythrocyte glutathione synthesis in adults with sickle cell disease, Am. J. Physiol. Endocrinol. Metab., 291(1):E73-9 (2006).

Risk factors for stroke and efficacy of antithrombotic therapy in atrial fibrillation. Analysis of pooled data from five randomized controlled trials, Arch. Intern. Med., 154(13):1449-57 (1994).

Roberts et al., Inhibition by adenosine of reactive oxygen metabolite production by human polymorphonuclear leucocytes, Biochem. J., 227(2):669-74 (1985).

Roberts et al., Isoprostanes, J. Lipid Res., 50 Suppl: S219-23 (2009).

Roger et al., Heart disease and stroke statistics—2011 update: a report from the American Heart Association, Circulation, 123(4):e18-e209 (2011).

Schoene et al., Genistein inhibits reactive oxygen species (ROS) production, shape change, and aggregation in rat platelets, Nutrition Res., 20(1):47-67 (2000).

Stringer, Tissue plasminogen activator inhibits reactive oxygen species production by macrophages, Pharmacotherapy, 20(4):375-9 (2000).

Turpie, Oral, direct factor Xa inhibitors in development for the prevention and treatment of thromboembolic diseases, Arterioscler. Thromb. Vasc. Biol., 27(6):1238-47 (2007).

Van Staa et al., A comparison of risk stratification schemes for stroke in 79,884 atrial fibrillation patients in general practice, J. Thromb. Haemost., 9(1):39-48 (2011).

Varma et al., Excretion of hydrogen peroxide in human urine, Free Radic. Res. Commun., 8(2):73-8 (1990).

Wang et al., A risk score for predicting stroke or death in individuals with new-onset atrial fibrillation in the community: the Framingham Heart Study, JAMA, 290(8):1049-56 (2003).

Diacron International, *The d-ROMs test: colorimetric determination of reactive oxygen metabolites*, Internet Archive Wayback Machine. Aug. 8, 2009. Dec. 24, 2013. http://web.archive.org/web/20090808175140/http:/www.diacron.com/htm/droms.htm.

\* cited by examiner hs-CRP, high sensitivity C-reactive protein; DROM, derivatives of reactive oxygen species; IL-1β, Interleukin Iβ; IL-6, Interleukin 6; TNF-α, Tumor necrosis factor-α; Iso-P, Isoprostanes Hs-CRP, high sensitivity C-reactive protein; DROM, derivatives of reactive proteins

METHODS OF DETERMINING NEED FOR ANTI-COAGULATION THERAPY

CROSS-REFERENCE TO RELATED APPLICATIONS

This application claims priority to International Patent Application No. PCT/US2011/045903, filed Jul. 29, 2011, which claims priority to U.S. Provisional Patent Application No. 61/368,941, filed on Jul. 29, 2010, each application which is incorporated herein by reference in its entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 4,064 bytes ACII (Text) file named "45994A_SeqListing.txt," created on Jul. 29, 2011.

BACKGROUND

Stroke is the most serious complication of longstanding atrial fibrillation (AF; *Circulation* 123(4): e18-e209 (Feb. 1, 2011); *Arch Intern Med* 154: 1449-1457 (1994)). Factors that are considered when determining a risk level of stroke for a patient include the patient's history of prior stroke or transient ischemic attack (TIA), presence of hypertension or diabetes, age greater than 75 years, and poor left ventricular function (*Arch Intern Med* 154: 1449-1457 (1994)). The identification of these factors led to the development of several risk stratification schemes (Gage, et al., *JAMA* 285(22): 2864-2870 (2001); Wang, et al., *JAMA* 290(8): 1049-1056 (2003)), including the CHADS2 risk scheme (Gage, et al., 2001, supra), where C stands for congestive heart failure, H for hypertension, A for age greater than or equal to 75 years, D for diabetes and S for prior strokes or TIAs. In the CHADS2 risk scheme, one point is assigned for the patient having a medical history of each of congestive heart failure, hypertension, age greater than or equal to 75 years, and diabetes, while two points are assigned when a patient has a history of TIA or stroke. It is believed that the frequency of stroke (adjusted stroke rate per 100 patient-years) increases as a CHADS2 score increases (Gage, et al., 2001, supra).

The $CHA_2DS_2$-VASc score represents another risk scheme used to determine risk level of stroke. In the $CHA_2DS_2$-VASc scheme, the same factors considered in the CHADS2 score are considered, but the $CHA_2DS_2$-VASc scheme additionally considers non-major stroke risk factors, including patient age between 65 and 74 years, female gender, and vascular disease.

While such risk stratification schemes have been found to be helpful in determining a patient's risk level for stroke and thus a patient's need for stroke prevention medication, e.g., anti-coagulation therapy, when the patient exhibits chronic AF, there nevertheless remains a need for a more accurate risk prediction model, especially in patients who fall in the intermediate risk category on these risk scores.

SUMMARY

The invention provides methods of determining a subject's need for stroke prophylaxis. The methods comprise the step of measuring a level of derivatives of reactive oxygen metabolites (DROMs) in a biological sample obtained from the subject, wherein an increased level of DROMs, relative to a control level, is indicative of the subject's need for stroke prophylaxis, e.g., anti-coagulation therapy.

In exemplary aspects, the invention is a method of determining a subject's need for anti-coagulation therapy, wherein the subject has a known CHADS2 or $CHA_2DS_2$-VASc score which is less than 2. The method comprises the step of measuring a level of DROMs in a biological sample obtained from the subject, wherein an increased level of DROMs, relative to a control level, is indicative of the subject's need for anti-coagulation therapy. If the level of DROMs is not increased, relative to a control level, the subject does not have a need for anti-coagulation therapy.

In exemplary aspects, the invention is a method of determining a subject's need for anti-coagulation therapy, wherein the method comprises the steps of: (i) determining a CHADS2 or $CHA_2DS_2$-VASc score of the subject; and (ii) measuring a level of DROMs, in a biological sample obtained from the subject, wherein a CHADS2 or $CHA_2DS_2$-VASc score of less than 2 and an increased level of DROMs, relative to a control level, is indicative of the subject's need for anti-coagulation therapy. If the level of DROMs is not increased, relative to a control level, the subject does not have a need for anti-coagulation therapy.

In exemplary aspects, the invention is a method of determining a subject's need for anti-coagulation therapy, wherein the subject exhibits atrial fibrillation or atrial flutter. The method comprises the step of measuring a level of DROMs in a biological sample obtained from the subject, wherein an increased level of DROMs, relative to a control level, is indicative of the subject's need for anti-coagulation therapy. If the level of DROMs is not increased, relative to a control level, the subject does not have a need for anti-coagulation therapy.

In exemplary aspects, the invention is a method of determining a subject's need for anti-coagulation therapy, wherein the method comprises the steps of measuring a level of DROMs and a level of C-reactive protein (hs-CRP) in a biological sample obtained from the subject. In this method, an increased level of DROMs and an increased level of hs-CRP, relative to a control level, is indicative of the subject's need for anti-coagulation therapy.

The invention also provides methods of determining a risk level of stroke for a subject. The methods comprise the step determining a stroke risk level according to a risk stratification scheme which accounts for the presence or absence of an increase in DROMs level, relative to a control, in the subject. In exemplary aspects, the presence of an increase in DROMs level, relative to a control, in the subject, contributes to an increased risk level of stroke of the subject.

The invention additionally provides a method of decreasing risk of stroke in a subject. The method comprises the steps of: (i) identifying the subject as a subject with a low to intermediate level of risk for stroke, (ii) identifying the subject as a subject with an increased level of DROMs relative to a control level, and (iii) administering an effective amount of an anti-coagulant to the subject, if the CHADS2 or CHA2DS2-VASc score is 2 or higher, or if the CHADS2 or CHA2DS2-VASc score is less than 2 and the level of DROMs is increased relative to a control level.

The invention further provides a method of determining the efficacy of a test agent as a stroke prophylactic agent. The method comprises the steps of (i) administering to a subject a test agent and (ii) measuring a level of C-reactive protein (hs-CRP), derivatives of reactive oxygen metabolites (DROMs), or both, in a biological sample obtained from the subject, wherein a decrease in the level of DROMs and/or hs-CRP, relative to the level prior to administration of the test agent, is indicative of the test agent as effective for decreasing risk of stroke in a subject.

The invention furthermore provides a method of monitoring a subject's risk of stroke. The method comprises the steps of: (i) measuring a level of C-reactive protein (hs-CRP), derivatives of reactive oxygen metabolites (DROMs), or both, in a biological sample obtained from the subject at a first time point, and (ii) comparing the level measured in step (i) to a level measured at a second time point, which occurs after the first time point, wherein a decreased level of DROMs and/or hs-CRP at the second time point relative to the first time point is indicative of a decrease in the subject's risk of stroke.

Further provided herein are kits comprising reagents for measuring a level of DROMs.

DETAILED DESCRIPTION

Figure 1:
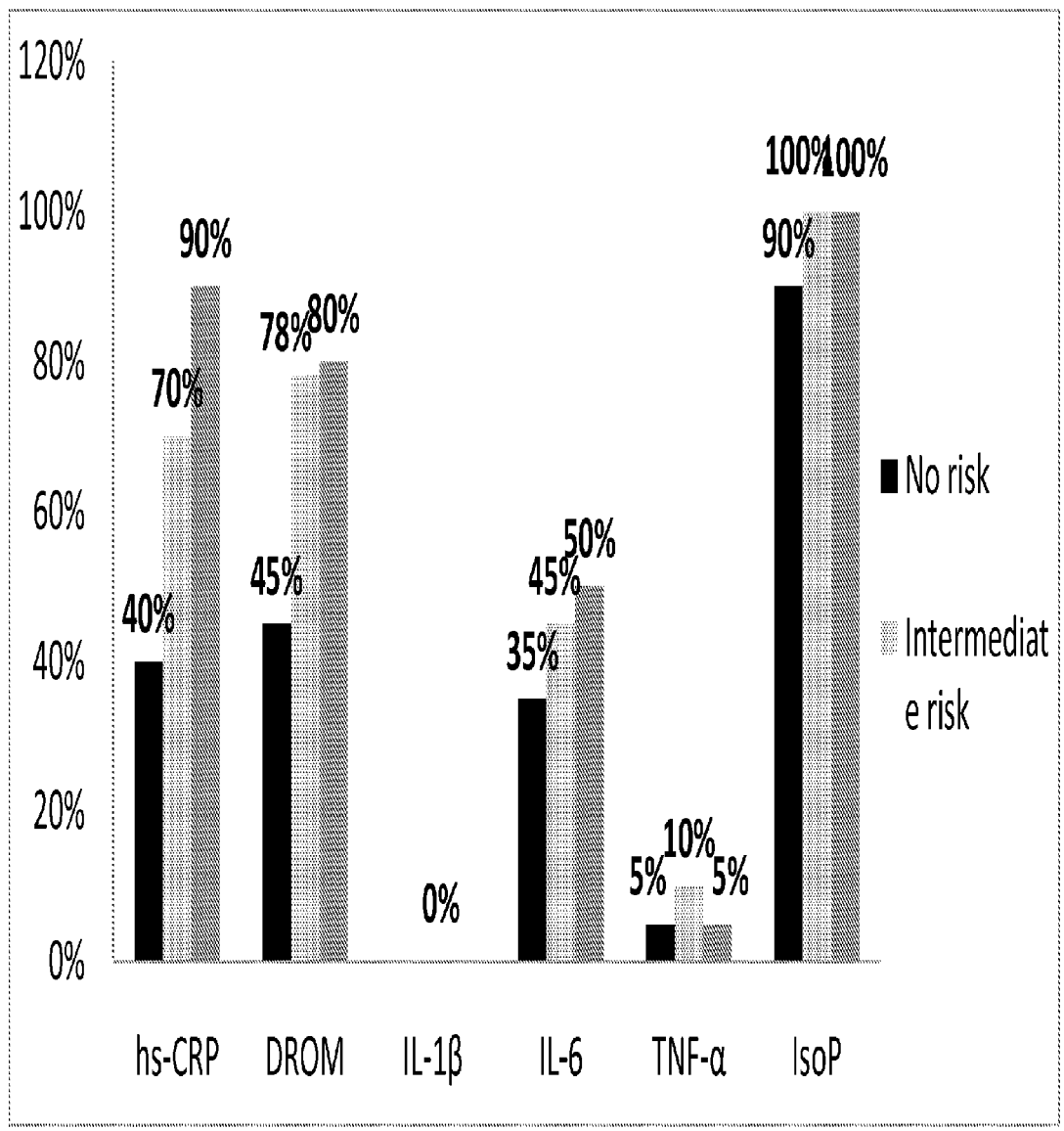
FIG. 1 is a graph of the percentage of patients participating in the study having the indicated CHADS2 level (0=No Risk; 1=Intermediate Risk; and 2=Severe Risk) that demonstrated abnormal levels of the indicated biomarker.

Methods of Determining a Subject's Need for Anti-Coagulation Therapy

The invention provides methods of determining a subject's need for stroke prophylaxis. The methods comprise the step of measuring a level of DROMs in a biological sample obtained from the subject, wherein an increased level of DROMs, relative to a control level, is indicative of the subject's need for stroke prophylaxis, e.g., anti-coagulation therapy.

As used herein, the term "stroke" is synonymous with "cerebrovascular accident" and refers to a rapidly-developing loss of brain function(s) due to disturbance in the blood supply to the brain.

As used herein, the term "DROMs" or "derivatives of reactive oxygen metabolites" or "D-ROMs" is synonymous with the term "ROMs" or "reactive oxygen metabolites" or "ROS" or "reactive oxygen species." DROMs include, for instance, the superoxide anion radical, hydroperoxyl radical, hydroxyl radical, hydrogen peroxide, and hypochlorous acid. In some embodiments, the DROM is a peroxide, e.g., any compound containing the peroxide anion ($O_2^{2-}$) or an oxygen-oxygen single bond. In some embodiments, the DROM is a free radical, e.g., an atom, molecule, or ion with unpaired elections on an open shell configuration. In some aspects, the DROM is a superoxide anion, hydrogen peroxide, hydroxyl radical, organic hydroperoxide, alkyoxy radical, peroxy radical, hypochlorous acid, peroxynitrite. DROMs includes molecules containing an oxygen atom with a partially empty outermost electron shell, which oxygen atoms are highly reactive. Due to their high reactivity, DROMs react with other molecules, e.g., other molecules in the body of a subject, frequently causing damage to these other molecules. Accordingly, in some embodiments, the DROM is a product compound or product molecule resulting from a DROM reacting with an organic substrate (e.g., carbohydrate, lipid, amino acid, protein, peptide, nucleotide, nucleic acid, etc.). In exemplary aspects, the DROM is a lipid peroxide, e.g., a peroxidized arachidonic acid.

Methods of measuring levels of DROMs in a biological sample are known in the art. See, for example, Neuman et al., *Clin Chem* 53(9): 1652-1657 (2007); Berliner et al., *Free Radic. Biol. Med.* 30:489-499 (2001); Varma and Devamanoharan, *Free Radic. Res. Commun.* 8:73-78 (1990); Long et al, *Biochem Biophys Res Commun* 262: 605-609 (1999); Kanaoka, et al., *Acta Med Okayama* 64(5): 223-230 (2010), Cornelli, et al., *J Nutr* 131: 3208-3211 (2001), Reid et al., *Am J Physiol Endocrinol Metab.* 291(1):E73-9. Epub 2006 Jan. 24, Halliwell and Whiteman, *Br J Pharmacol* 142(2): 231-255 (2004); and Example 1 set forth below. In some aspects, the level of DROMs is measured through spectrometry or chromatography, e.g., high-performance liquid chromatography (HPLC). In some aspects, the level of DROMs is measured through L-band electron spin resonance (ESR; Berliner et al., *Free Radic. Biol. Med.* 30:489-499 (2001)). In some aspects, the level of DROMs is measured using a commercially available kit, such as the d-ROMs test, sold by Diacron International s.r.l., (Grosetto, Italy).

As used herein, the term "subject" refers to a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perssodactyla, including Equines (horses), mammals from the order Primates, Ceboids, or Simoids (monkeys) and of the order Anthropoids (humans and apes). In exemplary aspects, the mammal is a human.

In exemplary aspects, the subject exhibits or suffers from cerebral vascular disease, congestive heart failure, carotid artery disease, cardiomyopathy, hypertension, diabetes, atrial fibrillation, atrial flutter. In exemplary aspects, the subject has a known CHADS2 or $CHA_2DS_2$-VASc score which is less than 2, e.g., 1,0.

The biological sample may be any sample (e.g., solid, liquid, or gas) obtained from the subject, including, but not limited to, exhaled air, breath condensate, tissue, cell extracts, whole blood, plasma, serum, inflammatory fluids, feces, urine, semen, cerebrospinal fluid, lymph (e.g., endolymph, perilymph), gastric juice, mucus, peritoneal fluid, pleural fluid, sebum, sweat, tears, vaginal secretion, vomit, breast milk, amniotic fluid, bile, cerumen, and saliva. In exemplary embodiments, the biological sample is whole blood, plasma, or serum.

In the methods of determining a subject's need for anti-coagulation therapy provided herein, an increased level of DROMs, relative to a control level, is indicative of the subject's need for stroke prophylaxis, e.g., anti-coagulation therapy. The increased level of DROMs is greater than a 10% increase, as compared to the control level. In exemplary embodiments, the increase in DROMs level is at least or about a 10% increase (e.g., at least or about a 20% increase, at least or about a 30% increase, at least or about a 40% increase, at least or about a 50% increase, at least or about a 60% increase, at least or about a 70% increase, at least or about a 80% increase, at least or about a 90% increase, at least or about a 95% increase, at least or about a 98% increase), relative to a control level.

In the methods of determining a subject's need for anti-coagulation therapy provided herein, if the measured level of DROMs is not increased, relative to a control level, the subject does not have a need for anti-coagulation therapy. For example, if the measured level of DROMs is the same or similar to a control level, the subject does not have a need for anti-coagulation therapy. In exemplary instances, a subject does not have a need for anti-coagulation therapy when the measured level of DROMs is decreased or is increased by no more than 10%, relative to a control level. In exemplary instances, the subject does not have a need for anti-coagulation therapy if the measured level of DROMs is increased by 10%, 9%, 8%, 7%, 6%, 5%, 4%, 3%, 2%, 1%, 0.5%, relative to a control level.

The level of DROMs may be compared to any suitable control level of DROMs representing a standard or normal state. For example, the control level to which the measured level of DROMs is compared may be an average or median level of DROMs of a population of subjects that are known to not have any risk of stroke, and, optionally, are matched to the subject in other parameters, such as one or more of the following: smoking status, age, presence of diabetes. Alternatively, the control level to which the measured level of DROMs is compared may be an absolute level of DROMs, e.g., 250 to 300 CARRATELLI UNITS (CARR U), wherein 1 CARR U corresponds to 0.08 mg/100 mL $H_2O_2$. In exemplary embodiments, the control level is a level which is less than or equal to 320 CARR U.

In exemplary aspects, the invention is a method of determining a subject's need for anti-coagulation therapy, wherein the subject has a known intermediate or low score of a stroke risk stratification scheme. The stroke risk stratification scheme may be any of those known in the art, including, but not limited to, the stroke risk stratification schemes described in Staa et al., *J Thromb Haemost* 9:39-48 (2011). In exemplary aspects, the stroke risk stratification scheme is the CHADS2 stroke risk stratification scheme or the $CHA_2DS_2$-VASc stroke risk stratification scheme, or a modified version thereof, e.g., a modified CHADS2 stroke risk stratification scheme. In exemplary aspects, the stroke risk stratification scheme is the National Institute for Health and Clinical Excellence stroke risk stratification scheme.

In exemplary aspects, the invention is a method of determining a subject's need for anti-coagulation therapy, wherein the subject has a known CHADS2 or $CHA_2DS_2$-VASc score which is less than 2. The method comprises the step of measuring a level of DROMs in a biological sample obtained from the subject, wherein an increased level of DROMs, relative to a control level, is indicative of the subject's need for anti-coagulation therapy. If the level of DROMs is not increased, relative to a control level, the subject does not have a need for anti-coagulation therapy.

In exemplary aspects, the subject has a known CHADS2 or $CHA_2DS_2$-VASc score of 1. In alternative aspects, the subject has a known CHADS2 or $CHA_2DS_2$-VASc score of 0. As used herein, the phrase "known CHADS2 or $CHA_2DS_2$-VASc score" refers to a CHADS2 or $CHA_2DS_2$-VASc score which was calculated prior to carrying out the method of determining a subject's need for anti-coagulation therapy (e.g., prior to measuring a level of derivatives of reactive oxygen metabolites (DROMs) in a biological sample obtained from the subject) and the score was recorded, e.g., in the subject's medical record, medical file, or medical history. In exemplary aspects, the known CHADS2 or $CHA_2DS_2$-VASc score was calculated within a year (e.g., within 11 months, within 10 months, within 9 months, within 8 months, within 7 months, within 6 months, within 5 months, within 4 months, within 3 months, within 2 months, within one month) prior to carrying out the method of determining a subject's need for anti-coagulation therapy (e.g., prior to measuring a level of DROMs in a biological sample obtained from the subject.

In exemplary aspects, the subject has a known CHADS2 or $CHA_2DS_2$-VASc score which is less than 2 and the subject exhibits atrial fibrillation or atrial flutter. The atrial fibrillation may be any form of AF, including any of those described herein. The atrial flutter may be any form of atrial flutter, including any of those described herein.

In exemplary aspects, the method further comprises measuring a level of CRP in a sample obtained from the subject. Methods of measuring CRP are known in the art, some of which is described herein.

In exemplary aspects, the invention is a method of determining a subject's need for anti-coagulation therapy, wherein the method comprises the steps of: (i) determining a stroke risk stratification scheme score of the subject; and (ii) measuring a level of DROMs, in a biological sample obtained from the subject, wherein a stroke risk stratification scheme score of low to intermediate and an increased level of DROMs, relative to a control level, is indicative of the subject's need for anti-coagulation therapy. If the level of DROMs is not increased, relative to a control level, the subject does not have a need for anti-coagulation therapy.

The stroke risk stratification scheme may be any of those known in the art, including, those described herein and in Staa et al., 2011, supra. In exemplary aspects, the stroke risk stratification scheme is the CHADS2 or $CHA_2DS_2$-VASc stroke risk stratification scheme. Accordingly, in exemplary aspects, the invention is a method of determining a subject's need for anti-coagulation therapy, wherein the method comprises the steps of: (i) determining a CHADS2 or $CHA_2DS_2$-VASc score of the subject; and (ii) measuring a level of DROMs, in a biological sample obtained from the subject, wherein a CHADS2 or $CHA_2DS_2$-VASc score of less than 2 and an increased level of DROMs, relative to a control level, is indicative of the subject's need for anti-coagulation therapy. If the level of DROMs is not increased, relative to a control level, the subject does not have a need for anti-coagulation therapy.

In exemplary aspects, step (i) comprises calculating a stroke risk stratification scheme score, e.g., a CHADS2 or $CHA_2DS_2$-VASc score. Methods of calculating a stroke risk stratification scheme, e.g., a CHADS2 or $CHA_2DS_2$-VASc score, are known in the art. See, e.g., Staa et al., 2011, supra, Gage, et al., 2001, supra, and Examples 1 and 2, set forth below. In alternative or additional aspects, step (i) comprises evaluating a subject's medical record, medical file, or medical history for a stroke risk stratification scheme score, e.g., a CHADS2 score or a $CHA_2DS_2$-VASc score.

The step of determining a stroke risk stratification scheme score, e.g., a CHADS2 or $CHA_2DS_2$-VASc score, of the subject and the step of measuring a level of DROMs may occur simultaneously (near simultaneously) or sequentially. In exemplary aspects, the step of determining a stroke risk stratification scheme score, e.g., a CHADS2 or $CHA_2DS_2$-VASc score, of the subject occurs before the step of measuring a level of DROMs, and in alternative aspects, the step of determining a stroke risk stratification scheme score, e.g., a CHADS2 or $CHA_2DS_2$-VASc score, of the subject occurs after the step of measuring a level of DROMs.

In exemplary aspects, the subject exhibits atrial fibrillation or atrial flutter. The atrial fibrillation may be any form of AF, including any of those described herein. The atrial flutter may be any form of atrial flutter, including any of those described herein.

In exemplary aspects, the method further comprises measuring a level of CRP in a sample obtained from the subject. Methods of measuring CRP are known in the art, some of which is described herein.

In exemplary aspects, the invention is a method of determining a subject's need for anti-coagulation therapy, wherein the subject exhibits atrial fibrillation or atrial flutter. The method comprises the step of measuring a level of DROMs in a biological sample obtained from the subject, wherein an increased level of DROMs, relative to a control level, is indicative of the subject's need for anti-coagulation therapy. If the level of DROMs is not increased, relative to a control level, the subject does not have a need for anti-coagulation therapy.

As used herein "atrial fibrillation" or "AF" refers to the absence of P waves and the presence of irregular intervals as determined by electrocardiography (ECG). In exemplary aspects, the AF is lone atrial fibrillation in which there is an absence of clinical or echocardiographic findings of other cardiovascular disease (including hypertension), related pulmonary disease, or cardiac abnormalities, such as enlargement of the left atrium, and age under 60 years. In exemplary aspects, the AF is nonvalvular AF in which there is an absence of rheumatic mitral valve disease, a prosthetic heart valve, or mitral valve repair. In exemplary aspects, the AF is secondary AF in which the AF occurs in the setting of a primary condition which may be the cause of the AF, such as acute myocardial infarction, cardiac surgery, pericarditis, myocarditis, hyperthyroidism, pulmonary embolism, pneumonia, or other acute pulmonary disease. In specific aspects, the atrial fibrillation is persistent atrial fibrillation. As used herein, the term "persistent atrial fibrillation" refers to recurrent episodes of AF that last more than 7 days. In specific aspects, the atrial fibrillation is paroxysmal atrial fibrillation. As used herein "paroxysmal atrial fibrillation" refers to recurrent episodes of AF that self-terminate in less than 7 days. In specific aspects, the atrial fibrillation is chronic atrial fibrillation. As used herein "chronic atrial fibrillation" refers to persistent AF that lasts for more than a year.

In exemplary aspects, the AF is AF that has been diagnosed in the subject by any routine study of pulse checks, ECGs, blood tests, echocardiography, chest X-ray, tranesophageal echocardiogram, Holter monitoring, exercise stress test, and the like.

In exemplary aspects, the AF is AF caused by hypertension, primary heart disease (including, e.g., coronary artery disease, mitral stenosis (e.g. due to rheumatic heart disease or mitral valve prolapse), mitral regurgitation, hypertrophic cardiomyopathy (HCM), pericarditis, congenital heart disease, previous heart surgery), lung diseases (e.g., pneumonia, lung cancer, pulmonary embolism, sarcoidosis), excessive alcohol consumption (e.g., "binge drinking" or "holiday heart syndrome"), hyperthyroidism, carbon monoxide poisoning, dual-chamber pacemakers in the presence of normal atrioventricular conduction, family history of AF, genetic mutations, or Friedreich's ataxia.

As used herein, the term "atrial flutter" refers to an abnormal heart rhythm that occurs in the atria of the heart. In exemplary aspects, the atrial flutter is a supra-ventricular tachycardia in which the subject's heart beats for more than 100 per minute. In exemplary aspects, the atrial flutter is a Type 1 atrial flutter, also known as a common atrial flutter and a typical atrial flutter, in which the atrial rate is 240 to 350 beats per minute. The Type 1 atrial flutter in some aspects is a counterclockwise atrial flutter. In other aspects, the Type 1 atrial flutter is a clockwise atrial flutters. In alternative aspects, the atrial flutter is a Type 2 atrial flutter in which the atrial rate is 340-350 beats per minute. In specific aspects, the atrial flutter is persistent atrial flutter. As used herein, the term "persistent atrial flutter" refers to recurrent episodes of atrial flutter that last more than 7 days. In specific aspects, the atrial flutter is paroxysmal atrial flutter. As used herein "paroxysmal atrial flutter" refers to recurrent episodes of atrial flutter that self-terminate in less than 7 days. In specific aspects, the atrial flutter is chronic atrial flutter. As used herein "chronic atrial flutter" refers to persistent atrial flutter that lasts for more than a year.

In exemplary aspects, the subject has a known low or intermediate stroke risk stratification scheme score, e.g., a CHADS2 or $CHA_2DS_2$-VASc score which is less than 2 (e.g., the subject has a known CHADS2 or $CHA_2DS_2$-VASc score of 1, the subject has a known CHADS2 or $CHA_2DS_2$-VASc score of 0).

In exemplary aspects, the method of determining a subject's need for anti-coagulation therapy, wherein the subject exhibits atrial fibrillation or atrial flutter, further comprises the step of determining a stroke risk stratification scheme score, e.g., a CHADS2 or $CHA_2DS_2$-VASc score, of the subject. In exemplary instances, the stroke risk stratification scheme score, e.g., the CHADS2 or $CHA_2DS_2$-VASc score, is determined by calculating a stroke risk stratification scheme score, e.g., a CHADS2 or $CHA_2DS_2$-VASc score. Methods of calculating a stroke risk stratification scheme score, e.g., a CHADS2 or $CHA_2DS_2$-VASc score, are described herein and in Staa et al., 2011, supra. In exemplary instances, the stroke risk stratification scheme score, e.g., the CHADS2 or $CHA_2DS_2$-VASc score, is determined by evaluating a subject's medical record for a stroke risk stratification scheme score, e.g., a CHADS2 score or a $CHA_2DS_2$-VASc score. In such cases, the subject has a known stroke risk stratification scheme score, e.g., a CHADS2 score or a $CHA_2DS_2$-VASc score, and the score was calculated and recorded at a time prior to the time that the level of DROMs is measured. In exemplary instances, the subject is determined to have a CHADS2 or $CHA_2DS_2$-VASc score which is less than 2, e.g., 1 or 0.

The step of determining a stroke risk stratification scheme score, e.g., a CHADS2 or $CHA_2DS_2$-VASc score, of the subject and the step of measuring a level of DROMs may occur simultaneously (near simultaneously) or sequentially. In exemplary aspects, the step of determining a stroke risk stratification scheme score, e.g., a CHADS2 or $CHA_2DS_2$-VASc score, of the subject occurs before the step of measuring a level of DROMs, and in alternative aspects, the step of determining a stroke risk stratification scheme score, e.g., a CHADS2 or $CHA_2DS_2$-VASc score, of the subject occurs after the step of measuring a level of DROMs.

In exemplary aspects, the method further comprises measuring a level of CRP in a sample obtained from the subject. Methods of measuring CRP are known in the art, some of which is described herein.

In exemplary aspects, the invention is a method of determining a subject's need for anti-coagulation therapy, wherein the method comprises the steps of measuring a level of DROMs and a level of C-reactive protein (hs-CRP) in a biological sample obtained from the subject. In this method, an increased level of DROMs and an increased level of hs-CRP, relative to a control level, is indicative of the subject's need for anti-coagulation therapy.

As used herein, the term "C-reactive protein" or "CRP" or "hs-CRP" refers to "high-sensitivity C reactive protein" which is a marker of inflammation. CRP binds to phosphocholine expressed on the surface of dead or dying cells (and some types of bacteria) in order to activate the complement system via the C1Q complex. In exemplary embodiments, the CRP comprises the amino acid sequence of SEQ ID NO: 1 or 2.

Levels of CRP may be measured by any suitable means known in the art, including, but not limited to immunoassay (e.g., ELISA, RIA), immunoturbidimetry, rapid immunodiffusion, laser nephelometry, and visual agglutination. In some aspects, the level of CRP is measured using a commercially available kit (e.g., Fluorokine® MAP Human C-Reactive Protein (CRP) Kit), antibodies, ELISAs (e.g., Quantikine® Human C-Reactive Protein Immunoassay), such as, for example, those sold by R&D Systems (Minneapolis, Minn.).

In the methods of determining a subject's need for anti-coagulation therapy provided herein, an increased level of CRP, relative to a control level, is indicative of the subject's need for stroke prophylaxis, e.g., anti-coagulation therapy. The increased level of CRP is greater than a 10% increase, as compared to the control level. In exemplary embodiments, the increase in CRP level is at least or about a 10% increase (e.g., at least or about a 20% increase, at least or about a 30% increase, at least or about a 40% increase, at least or about a 50% increase, at least or about a 60% increase, at least or about a 70% increase, at least or about a 80% increase, at least or about a 90% increase, at least or about a 95% increase, at least or about a 98% increase), relative to a control level.

In the methods of determining a subject's need for anti-coagulation therapy provided herein, if the measured level of CRP is not increased, relative to a control level, the subject does not have a need for anti-coagulation therapy. For example, if the measured level of CRP is the same or similar to a control level, the subject does not have a need for anti-coagulation therapy. In exemplary instances, a subject does not have a need for anti-coagulation therapy when the measured level of CRP is decreased or is increased by no more than 10%, relative to a control level. In exemplary instances, the subject does not have a need for anti-coagulation therapy if the measured level of CRP is increased by 10%, 9%, 8%, 7%, 6%, 5%, 4%, 3%, 2%, 1%, 0.5%, relative to a control level.

The level of CRP may be compared to any suitable control level of CRP representing a standard or normal state. For example, the control level to which the measured level of CRP is compared may be an average level of CRP of a population of subjects that are known to not have any risk of stroke, and, optionally, are matched to the subject in other parameters, such as one or more of the following: smoking status, age, presence of diabetes. Alternatively, the control level to which the measured level of CRP is compared may be an absolute level of CRP, e.g., less than 10 µg/ml (e.g., less than 5 µg/ml, less than 4 µg/ml). For example, the control level to which the measured level of CRP is compared may be <3 µg/L. Also, for example, the control level may be the normal concentration found in healthy human serum, which is usually lower than 10 mg/L, and which slightly increases with age. Also, the control level of CRP may be determined taking into account that higher levels are found in late pregnant women, mild inflammation and viral infections (10-40 mg/L), active inflammation, bacterial infection (40-200 mg/L), severe bacterial infections and burns (>200 mg/L).

The biological sample in which the level of CRP is measured may be the same biological sample in which the level of DROMs is measured. In alternative aspects, the biological sample in which the level of CRP is measured is a different biological sample in which the level of DROMs is measured. When the method comprises both steps of measuring the level of CRP and measuring the level of DROMs, the steps may occur simultaneously or sequentially. In some aspects, the step of measuring the level of CRP occurs before the step of measuring the level of DROMs. In alternative aspects, the step of measuring the level of CRP occurs after the step of measuring the level of DROMs.

In exemplary aspects, the subject exhibits atrial fibrillation or atrial flutter. The atrial fibrillation may be any form of AF, including any of those described herein. The atrial flutter may be any form of atrial flutter, including any of those described herein.

In exemplary aspects, the subject has a known low to intermediate stroke risk stratification scheme score, e.g., a CHADS2 or $CHA_2DS_2$-VASc score which is less than 2 (e.g., the subject has a known CHADS2 or $CHA_2DS_2$-VASc score of 1, the subject has a known CHADS2 or $CHA_2DS_2$-VASc score of 0).

In exemplary aspects, the method of determining a subject's need for anti-coagulation therapy, wherein the subject exhibits atrial fibrillation or atrial flutter, further comprises the step of determining a stroke risk stratification scheme score, e.g., a CHADS2 or $CHA_2DS_2$-VASc score, of the subject. In exemplary instances, the stroke risk stratification scheme score, e.g., the CHADS2 or $CHA_2DS_2$-VASc score, is determined by calculating a stroke risk stratification scheme score, e.g., a CHADS2 or $CHA_2DS_2$-VASc score. Methods of calculating a stroke risk stratification scheme score, e.g., a CHADS2 or $CHA_2DS_2$-VASc score, are described herein and Staa et al., 2011, supra. In exemplary instances, the stroke risk stratification scheme score, e.g., the CHADS2 or $CHA_2DS_2$-VASc score, is determined by evaluating a subject's medical record for a stroke risk stratification scheme score, e.g., a CHADS2 score or a $CHA_2DS_2$-VASc score. In such cases, the subject has a known stroke risk stratification scheme score, e.g., a CHADS2 score or a $CHA_2DS_2$-VASc score, and the score was calculated and recorded at a time prior to the time that the level of DROMs is measured. In exemplary instances, the subject is determined to have a CHADS2 or $CHA_2DS_2$-VASc score which is less than 2, e.g., 1 or 0.

Methods of Determining Risk of Stroke

The invention also provides methods of determining a risk level of stroke for a subject. The methods comprise the step determining a stroke risk level according to a risk stratification scheme which accounts for the presence or absence of an increase in DROMs level, relative to a control, in the subject. In exemplary aspects, the presence of an increase in DROMs level, relative to a control, in the subject, contributes to an increased risk level of stroke of the subject.

In exemplary aspects, the method comprises the step of measuring a level of DROMs in a biological sample obtained from the subject. The level of DROMs may be measured through any technique known in the art, including any of those described herein.

In exemplary aspects, the method comprises determining a CHADS2 score of the subject. Accordingly, in exemplary aspects, a risk level of stroke for a subject is determined, per the risk stratification scheme, as outlined below:

| Condition | Points |
| --- | --- |
| Congestive heart failure | 1 |
| Hypertension: blood pressure consistently above 140/90 mmHg (or treated hypertension on medication) | 1 |
| Age ≥75 years | 1 |
| Diabetes mellitus | 1 |
| Increased DROMs level | 1 |
| Prior Stroke or TIA | 2 |

In exemplary aspects, the method comprises the step of determining a stroke risk level according to a risk stratification scheme which accounts for the presence or absence of an increase in DROMs level, relative to a control, in the subject, and for the presence or absence of an increase in CRP level, relative to a control, in the subject. In exemplary aspects, the presence of an increase in DROMs level, relative to a control, in the subject, and/or the presence of an increase in CRP level, relative to a control, in the subject, contributes to an increased risk level of stroke of the subject.

In exemplary aspects, the method comprises the step of measuring a level of DROMs in a biological sample obtained from the subject. The level of DROMs may be measured through any technique known in the art, including any of those described herein.

In exemplary aspects, the method comprises the step of measuring a level of CRP in a biological sample obtained from the subject. The level of CRP may be measured through any technique known in the art, including any of those described herein.

In exemplary aspects, the method comprises determining a CHADS2 score of the subject. Accordingly, in exemplary aspects, a risk level of stroke for a subject is determined, per the risk stratification scheme, as outlined below:

| Condition | Points |
|---|---|
| Congestive heart failure | 1 |
| Increased CRP level | 1 |
| Hypertension: blood pressure consistently above 140/90 mmHg (or treated hypertension on medication) | 1 |
| Age ≥75 years | 1 |
| Diabetes mellitus | 1 |
| Increased DROMs level | 1 |
| Prior Stroke or TIA | 2 |

In exemplary aspects, the method comprises determining a subject's need for anti-coagulation therapy, according to the risk level stratification scheme, as outlined in either of the two tables below:

| CHADS2 score | DROMs level (relative to a control level) | DROMs/CHADS2 Risk Level of Stroke | Need for anti-coagulation therapy? |
|---|---|---|---|
| 0 | No increase | A | No |
| 0 | Increased | B | Yes |
| 1 | No increase | C | No |
| 1 | Increased | D | Yes |
| 2 | Increased | E | Yes |
| 3 | Increased | F | Yes |
| 4 | Increased | G | Yes |
| 5 | Increased | H | Yes |
| 6 | Increased | I | Yes |

| CHADS2 score | CRP and/or DROMs level (relative to a control level) | DROMs/CRP/CHADS2 Risk Level of Stroke | Need for anti-coagulation therapy? |
|---|---|---|---|
| 0 | No increase | A | No |
| 0 | Increased | B | Yes |
| 1 | No increase | C | No |
| 1 | Increased | D | Yes |
| 2 | Increased | E | Yes |
| 3 | Increased | F | Yes |
| 4 | Increased | G | Yes |
| 5 | Increased | H | Yes |
| 6 | Increased | I | Yes |

Methods of Decreasing Risk of Stroke

The invention further provides methods of decreasing risk of stroke in a subject. In exemplary aspects, the method comprises the steps of: (i) identifying the subject as a subject with a low to intermediate level of risk for stroke, (ii) identifying the subject as a subject with an increased level of derivatives of reactive oxygen metabolites (DROMs) relative to a control level, and (iii) administering an effective amount of an anti-coagulant to the subject, if the CHADS2 or $CHA_2DS_2$-VASc score is 2 or higher, or if the CHADS2 or $CHA_2DS_2$-VASc score is less than 2 and the level of DROMs is increased relative to a control level.

In exemplary aspects, step (i) of the method comprises: (a) determining a level of risk for stroke by considering the subject's age and evaluating the subject's medical record for evidence of hypertension, diabetes, heart failure, prior stroke, or prior transient ischemic attack (TIA), (b) evaluating a subject's medical record for a stroke risk stratification scheme score, e.g., a CHADS2 score or a $CHA_2DS_2$-VASc score, (c) calculating a stroke risk stratification scheme score, e.g., a CHADS2 or $CHA_2DS_2$-VASc score, of the subject, or any combination of (a)-(c), e.g., a combination of (a), (b), and (c), or a combination of (a) and (b), or a combination of (a) and (c), or a combination of (b) and (c).

In exemplary aspects, step (ii) of the method comprises: (a) measuring a level of DROMs in a biological sample obtained from the subject, (b) evaluating the subject's medical record for increased levels of DROMs, or both of (a) and (b).

Any permutation of the options for step (i) and the options for step (ii) are contemplated for purposes of the invention. For example, the method may comprise (a) of step (i) and (a) of step (ii); or (a) of step (i) and (b) of step (ii); or (a) of step (i) and both (a) and (b) of step (ii); or (b) of step (i) and (a) of step (ii); or (b) of step (i) and (b) of step (ii); or (b) of step (i) and both (a) and (b) of step (ii); (c) of step (i) and (a) of step (ii); or (c) of step (i) and (b) of step (ii); or (c) of step (i) and both (a) and (b) of step (ii); or both (a) and (b) of step (i) and (a) of step (ii); or both (a) and (b) of step (i) and (b) of step (ii); or both (a) and (b) of step (i) and both (a) and (b) of step (ii); or both (a) and (c) of step (i) and (a) of step (ii); or both (a) and (c) of step (i) and (b) of step (ii); or both (a) and (c) of step (i) and both (a) and (b) of step (ii); or both (c) and (b) of step (i) and (a) of step (ii); or both (c) and (b) of step (i) and (b) of step (ii); or both (c) and (b) of step (i) and both (a) and (b) of step (ii); or all of (a) to (c) of step (i) and (a) of step (ii); or all of (a) to (c) of step (i) and (b) of step (ii); or all of (a) to (c) of step (i) and both (a) and (b) of step (ii).

The step of administering an effective amount of an anti-coagulant to the subject may occur through any suitable route of administration known in the art, some of which are described herein. In exemplary aspects, the step of administering an effective amount of an anti-coagulant to the subject comprises orally administering an anti-coagulant to the subject.

The anti-coagulant administered to the subject may be any suitable substance that prevents coagulation (e.g., blood clotting) known in the art, some of which are described herein without limitation. In exemplary embodiments, also without limitation, the anti-coagulant administered to the subject is an oral anti-coagulant. In exemplary aspects, without limitation, the anti-coagulant is Coumadin (warfarin) or dabigatran.

In exemplary aspects, the method further comprises measuring a level of CRP in a sample obtained from the subject. Methods of measuring CRP are known in the art, some of which is described herein. In exemplary aspects, the method further comprises the step of evaluating the subject's medical record for increased levels of hsCRP.

In exemplary embodiments, the decrease of stroke risk provided by the methods of the invention is at least or about a 10% decrease, at least or about a 20% decrease, at least or about a 30% decrease, at least or about a 40% decrease, at least or about a 50% decrease, at least or about a 60% decrease, at least or about a 70% decrease, at least or about a 80% decrease, at least or about a 90% decrease, at least or about a 95% decrease, or at least or about a 98% decrease.

One of ordinary skill in the art will recognize that the method of decreasing risk of stroke in a subject is essentially the same as a method of preventing stroke in a subject. As used herein, the term "prevent" and words stemming therefrom encompasses delaying the onset of the medical condition being prevented. In exemplary aspects, the method delays the onset of the medical condition by 1 day, 2 days, 4 days, 6 days, 8 days, 10 days, 15 days, 30 days, two months, 4 months, 6 months, 1 year, 2 years, 4 years, or more. As used herein, the term "prevent" and words stemming therefrom encompasses reducing the risk of the medical condition being prevented. In exemplary aspects, the method reduces the risk of stroke 2-fold, 5-fold, 10-fold, 20-fold, 50-fold, 100-fold, or more.

Methods of Monitoring Risk of Stroke

The invention further provides methods of monitoring a subject's risk of stroke. In exemplary aspects, the method comprises the steps of: (i) measuring a level of CRP, DROMs, or both, in a biological sample obtained from the subject at a first time point, and (ii) comparing the level measured in step (i) to a level measured at a second time point, which occurs after the first time point, wherein a decreased level of DROMs and/or hs-CRP at the second time point relative to the first time point is indicative of a decrease in the subject's risk of stroke. In exemplary aspects, the method comprises measuring a level of DROMs in the biological sample, and optionally comprises measuring CRP in a biological sample. In exemplary aspects, the method does not comprise the step of measuring CRP in a biological sample.

Methods of measuring DROMs and CRP levels are described in the art and herein. In exemplary embodiments, the decreased level of DROMs and/or CRP is at least or about a 10% decrease, at least or about a 20% decrease, at least or about a 30% decrease, at least or about a 40% decrease, at least or about a 50% decrease, at least or about a 60% decrease, at least or about a 70% decrease, at least or about a 80% decrease, at least or about a 90% decrease, at least or about a 95% decrease, or at least or about a 98% decrease.

In exemplary aspects, the first time point occurs before an event and the second time point occurs after the event. In exemplary instances, the event is a first time administration of an anti-coagulant, such that an anti-coagulant is administered to the subject for the first time after the first time point but before the second time point. Accordingly, the method may be considered as a method of determining the efficacy of the anti-coagulant in the subject as it pertains to risk of stroke.

In alternative aspects, the subject is following an anti-coagulation therapeutic regimen, and the event is a change in the therapeutic regimen. In exemplary aspects, the change is an increase in dose of an anti-coagulant, and the method may be considered a method of determining the efficacy of the increased dose of anti-coagulant in the subject as it pertains to risk of stroke. In further exemplary aspects, the change is a decrease in dose of an anti-coagulant, and the method may be considered a method of determining the efficacy of the decreased dose of anti-coagulant in the subject as it pertains to risk of stroke. In such aspects, a maintained level of DROMs and/or hs-CRP at the second time point relative to the first time point is indicative of the efficacy of the decreased dose of the anti-coagulant in the subject as it pertains to risk of stroke. In additional exemplary aspects, the change is a substitution of one anti-coagulant agent to another anti-coagulant agent, and the method may be considered a method of determining the efficacy of the new anti-coagulant in the subject as it pertains to risk of stroke. In yet other aspects, the change is an addition of an anti-coagulant to the therapeutic regimen, and the method may be considered a method of determining the efficacy of the combination of the anti-coagulants in the subject as it pertains to risk of stroke. In other aspects, the change is a deletion of an anti-coagulant from the therapeutic regimen and, the method may be considered a method of determining the risk of stroke in the absence of the deleted anti-coagulant. In exemplary embodiments, the change may be any combination of the aforementioned changes.

In exemplary aspects, the subject exhibits atrial fibrillation or atrial flutter. The atrial fibrillation may be any form of AF, including any of those described herein. The atrial flutter may be any form of atrial flutter, including any of those described herein.

Determining Efficacy of Therapeutic Agents

The invention also provides methods of determining the efficacy of a therapeutic agent. In exemplary aspects, the method comprises the steps of (i) administering to a subject a therapeutic agent and (ii) measuring a level of C-reactive protein (hs-CRP), derivatives of reactive oxygen metabolites (DROMs), or both, in a biological sample obtained from the subject, wherein a decrease in the level of DROMs and/or hs-CRP, relative to the level prior to administration of the therapeutic agent, is indicative of the therapeutic agent as effective for decreasing risk of stroke in a subject. In exemplary aspects, the method comprises measuring a level of DROMs in the biological sample, and optionally comprises the step of measuring CRP in a biological sample. In exemplary aspects, the method does not comprise the step of measuring CRP in a biological sample.

The step of administering an effective amount of a therapeutic agent to the subject occurs through any suitable route of administration known in the art, some of which are described herein. In exemplary aspects, the step of administering an effective amount of a therapeutic agent to the subject comprises orally administering a therapeutic agent to the subject.

The therapeutic agent may be any suitable agent and in exemplary aspects is a therapeutic agent which is being evaluated for its efficacy as a stroke prophylactic. In some aspects, the therapeutic agent is a therapeutic agent which is not known as a stroke prophylactic agent. In some aspects, the therapeutic agent is a derivative or analog of a known stroke prophylactic, e.g., a known anti-coagulant. In some aspects, the therapeutic agent is a known stroke prophylactic, e.g., anti-coagulant, and the method determines the efficacy of the known stroke prophylactic in a particular subject or patient population. In exemplary aspects, the anti-coagulant administered to the subject is an oral anti-coagulant. In exemplary aspects, the anti-coagulant is Coumadin (warfarin) or dabigatran.

In exemplary embodiments, the method further comprises the step of measuring a level of C-reactive protein (hs-CRP), derivatives of reactive oxygen metabolites (DROMs), or both, in a biological sample obtained from the subject before administering the therapeutic agent to the subject.

Methods of measuring DROMs and CRP levels are described in the art and herein. In exemplary embodiments, the decreased level of DROMs and/or CRP is at least or about a 10% decrease, at least or about a 20% decrease, at least or about a 30% decrease, at least or about a 40% decrease, at least or about a 50% decrease, at least or about a 60% decrease, at least or about a 70% decrease, at least or about a 80% decrease, at least or about a 90% decrease, at least or about a 95% decrease, or at least or about a 98% decrease.

In exemplary aspects, the subject exhibits atrial fibrillation or atrial flutter. The atrial fibrillation may be any form of AF, including any of those described herein. The atrial flutter may be any form of atrial flutter, including any of those described herein.

Steps of the Methods of the Invention

The methods of the invention optionally comprise additional steps, as noted herein, or as otherwise appreciated by the ordinarily skilled artisan. For example, the methods of the invention optionally comprise, unless noted otherwise, one or more of the following steps: (i) determining a CHADS2 score or CHASC2DS2-Vasc score of the subject, (ii) measuring a level of CRP in a biological sample obtained from the subject, and (iii) administering to the subject an effective amount of an anti-coagulant. The methods optionally comprise measuring the levels of additional markers of inflammation or oxidative stress. For example, the methods optionally comprise measuring the level of Interleukin-1β, Interleukin-6, TNFα, or isoprostanes.

In cases in which a method comprises combination of steps, each and every combination or sub-combination of the steps is encompassed within the scope of the invention, unless otherwise noted herein.

In regards to any of the methods of the invention, the steps of the method may occur simultaneously or sequentially. When the steps of the method occur sequentially, the steps may occur in any order, unless noted otherwise.

Kits

The invention furthermore provides kits comprising reagents for measuring a level of DROMs and information, or access thereto, correlating a DROMs level to risk level of stroke or to need for anti-coagulation. In exemplary aspects, the kit comprises a DROM-reactive chromogenic substrate (e.g., a chromogenic substrate that changes color when reacted with a DROM, e.g., a hydroperoxide). In exemplary aspects, the information is provided on a paper included in the kit or via an electronic medium, e.g., a compact disc, a flash drive, a diskette. In exemplary aspects, the information is provided by way of providing directions to an internet site at which the information may be accessed by the user. In exemplary aspects, the information is provided to the user after submitting, e.g., by mail or by phone, the measured DROMs levels. In some aspects, the kit comprises an electronic copy of a computer software program which allows the user to compare the DROMs level with that of a control level.

In exemplary aspects, the kit further comprises reagents for a measuring a level of CRP and information, or access thereto, correlating a CRP level to risk level of stroke or to need for anti-coagulation. In exemplary instances, the kit comprises a CRP binding agent, e.g., a CRP-specific antibody, a CRP ELISA.

In exemplary aspects, the kit further comprises instructions for determining a CHADS2 or $CHA_2DS_2$-VASc score. In exemplary aspects, the instructions are provided on a paper included in the kit or via an electronic medium, e.g., a compact disc, a flash drive, a diskette. In exemplary aspects, the instructions are provided by way of providing directions to an internet site at which the instructions may be accessed by the user.

In exemplary aspects, the kit further comprises an anti-coagulant and information, or access thereto, correlating a DROMs level to need for anti-coagulation therapy.

In exemplary aspects, the kit further comprises a unit for a collecting a sample, e.g., any of the samples described herein, of the subject. In some aspects, the unit for collecting a sample is a vial, a beaker, a tube, a microtiter plate, a petri dish, and the like. In exemplary embodiments, the unit comprises reagents that prevent rapid oxidation of the sample. The unit may comprise, for example, any one or more of the following: L-serine borate, sodium heparin, bathophenanthroline disulfonate sodium salt, and iodoacetic acid.

Anti-Coagulation Therapy

As used herein, the term "anti-coagulation therapy" means a therapeutic regiment comprising an anti-coagulant. As used herein, the term "anti-coagulant" means a substance that prevents coagulation (blood clotting). The anti-coagulant may be any of those known in the art, including, but not limited to: vitamin K antagonists, Coumadin, (warfarin), acenocoumarol, phenprocoumon, brodifacoum, phenindione, heparin, low molecular weight heparin, fondaparinux, idraparinux, direct thrombin inhibitor (e.g., argatroban, lepirudin, vialirudin, dabigatran), batroxobin, hementin, nattokinase, or lumbrokinase. The anti-coagulant may be a direct reactive oxygen metabolite inhibitor, e.g., adenosine (Roberts et al., *Biochem J* 227: 669-674 (1985)), dexamethasone (Huo et al., *BMC Neuroscience* 12: 49-67 (2011)); genistein (Schoene and Guidry, *Nutrition Res* 20(1): 47-57 (2000)); and tissue plasminogen activator (TPA; Stringer, *Pharmacotherapy* 20: 375-379 (2000)). The anti-coagulant may be a Factor X inhibitor or a Direct Factor Xa inhibitor ("xabans"), e.g., apixaban, edoxaban, otamixaban, rivaroxaban, and YM466, described in Turpie, *Arterioscler. Thromb. Vasc. Biol.* 27 (6): 1238-47 (2007); Cohen et al., *Circulation* 115 (20): 2642-51 (2007); Paccaly et al., *Thromb. Haemost.* 94 (6): 1156-63. (2005); Eriksson et al., *Circulation* 114(22): 2374-2381 (2006); and Iwatsuki et al., *Biol Pharm Bull* 30: 1874-1877 (2007).

Routes of Administration

In some embodiments of the methods provided herein, the method comprises the step of administering an effective amount of an anti-coagulant to the subject. The anti-coagulant may be administered to the subject via any suitable route of administration. The following discussion on routes of administration is merely provided to illustrate exemplary embodiments and should not be construed as limiting the scope in any way.

Formulations suitable for oral administration can consist of (a) liquid solutions, such as an effective amount of the active agent of the present disclosure dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the anti-coagulant in a flavor, usually sucrose and acacia or tragacanth, as well as pastilles comprising the anti-coagulant in an inert base, such as gelatin and glycerin, or sucrose and acacia, emulsions, gels, and the like containing, in addition to, such excipients as are known in the art.

The anti-coagulant, alone or in combination with other suitable components, can be delivered via pulmonary administration and can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa. In some embodiments, the anti-coagulant is formulated into a powder blend or into microparticles or nanoparticles. Suitable pulmonary formulations are known in the art. See, e.g., Qian et al., Int J Pharm 366: 218-220 (2009); Adjei and Garren, Pharmaceutical Research, 7(6): 565-569 (1990); Kawashima et al., J Controlled Release 62(1-2): 279-287 (1999); Liu et al., Pharm Res 10(2): 228-232 (1993); International Patent Application Publication Nos. WO 2007/133747 and WO 2007/141411.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term, "parenteral" means not through the alimentary canal but by some other route such as subcutaneous, intramuscular, intraspinal, or intravenous. The anti-coagulant may be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-153-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations in some embodiments contain from about 0.5% to about 25% by weight of the anti-coagulant in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations in some aspects are presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions in some aspects are prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Additionally, the anti-coagulant may be made into suppositories for rectal administration by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that the anti-coagulant may be formulated as inclusion complexes, such as cyclodextrin inclusion complexes, or liposomes.

Dosages

For purposes of the disclosure, the effective amount or dose of the anti-coagulant administered should be sufficient to provide a therapeutic or prophylactic response in the subject or animal over a reasonable time frame. For example, the dose of the anti-coagulant should be sufficient to decrease risk of stroke as described herein in a period of from about 1 to 4 minutes, 1 to 4 hours or 1 to 4 weeks or 5 to 20 or more weeks, from the time of administration. In certain embodiments, the time period is even longer. The dose will be determined by the efficacy of the particular active agent and the condition of the animal (e.g., human), as well as the body weight of the animal (e.g., human) to be treated.

Many assays for determining an administered dose are known in the art. For purposes herein, an assay, which comprises comparing the extent to which stroke risk is decreased upon administration of a given dose of the anti-coagulant to a mammal among a set of mammals, each set of which is given a different dose of the anti-coagulant, could be used to determine a starting dose to be administered to a mammal. The extent to which stroke risk is decreased upon administration of a certain dose can be represented by, for example, a decrease in DROMs, relative to a control level. Methods of measuring DROMs are known in the art, including, for instance, the methods described in the EXAMPLES set forth below.

The dose of the anti-coagulant also will be determined by the existence, nature and extent of any adverse side effects that might accompany the administration of a particular anti-coagulant. Typically, the attending physician will decide the dosage of the anti-coagulant with which to treat each individual patient, taking into consideration a variety of factors, such as age, body weight, general health, diet, sex, anti-coagulant to be administered, route of administration, and the severity of the condition being treated. By way of example and not intending to limit the invention, the dose of the anti-coagulant can be about 0.0001 to about 1 g/kg body weight of the subject being treated/day, from about 0.0001 to about 0.001 g/kg body weight/day, or about 0.01 mg to about 1 g/kg body weight/day.

Controlled Release Formulations

In some embodiments, the anti-coagulants described herein can be modified into a depot form, such that the manner in which the anti-coagulant is released into the body to which it is administered is controlled with respect to time and location within the body (see, for example, U.S. Pat. No. 4,450,150). Depot forms of anti-coagulant may be, for example, an implantable composition comprising the anti-coagulant and a porous or non-porous material, such as a polymer, wherein the anti-coagulant is encapsulated by or diffused throughout the material and/or degradation of the non-porous material. The depot is then implanted into the desired location within the body of the subject and the anti-coagulant is released from the implant at a predetermined rate.

The anti-coagulant in certain aspects is modified to have any type of in vivo release profile. In some aspects, the anti-coagulant is modified to provide an immediate release, controlled release, sustained release, extended release, delayed release, or bi-phasic release of the active agent. Methods of formulating compounds for controlled release are known in the art. See, for example, Qian et al., *J Pharm* 374: 46-52 (2009) and International Patent Application Publication Nos. WO 2008/130158, WO2004/033036; WO2000/032218; and WO 1999/040942.

The anti-coagulant may further comprise, for example, micelles or liposomes, or some other encapsulated form, or may be administered in an extended release form to provide a prolonged storage and/or delivery effect.

Timing of Administration

The anti-coagulant may be administered according to any regimen including, for example, daily (including but not limited to 1 time per day, 2 times per day, 3 times per day, 4 times per day, 5 times per day, 6 times per day), every two days, every three days, every four days, every five days, every six days, weekly, bi-weekly, every three weeks, monthly, or bi-monthly. Timing, like dosing is adjusted based on dose-response studies, efficacy, and toxicity data, and initially gauged based on timing used for other antibody therapeutics.

Combinations

In some embodiments, the anti-coagulants are administered alone, and in alternative embodiments, the anti-coagulants are administered in combination with another therapeutic agent, e.g., another active agent of the invention of different type (e.g., structure). In some aspects, the other therapeutic aims to treat or prevent atrial fibrillation or atrial flutter, diabetes, hypertension, TIAs, and/or high cholesterol.

In exemplary embodiments, the active agent is administered simultaneously as the other therapeutic. In alternative embodiments, the active agent is administered either before or after the other therapeutic.

The following examples are given merely to illustrate the present invention and not in any way to limit its scope.

EXAMPLES

Example 1

Consecutive subjects with electrocardiographically (ECG)-documented chronic AF were enrolled from clinics at the Atlanta Veterans Affairs Medical Center and Emory University Affiliated hospitals. The study protocol was approved by the respective Institutional Review Boards. AF was defined as the absence of P waves and irregular RR intervals on ECG. Chronic AF was defined as persistent AF for more than a year. Exclusion criteria included age <18 years, paroxysmal AF, hemodynamic instability, thyroid disorders, uncontrolled hypertension (blood pressure>180/100 at rest), presence of inflammatory condition or malignancies. Medical records were reviewed for baseline demographic and clinical data including presence of cardiovascular disease, hypertension, and diabetes, history of strokes or TIAs and concomitant medications.

CHADS-2 score was calculated for each subject by assigning one point for age >75 years, hypertension, diabetes and heart failure, and two points for history of prior stroke or TIA. Hypertension was defined either by historical documentation, readings obtained of systolic blood pressure ≥140 mmHg and/or diastolic blood pressure ≥90 mmHg, or the use of antihypertensive medication. Diabetes was present if reported by a physician or the patient was using anti-diabetic agents and/or insulin. The presence of heart failure was determined either from the medical records or by an ejection fraction of less than 45% on a recent echocardiogram. History of stroke or TIA was determined from the medical records.

Plasma levels of markers of inflammation and oxidative stress were measured in a non-fasting state. Abnormal levels were defined using the upper limit of normal reference range as a cut off, wherein the normal reference ranges were as follows:

| Marker | TNFα  | IL-6  | IL-1  | hsCRP  | DROM       | Isoprostanes |
|--------|-------|-------|-------|--------|------------|--------------|
| Levels | <8    | <5    | <3    | <3     | 250-300    | 351-685      |
| Units  | Pg/ml | Pg/ml | Pg/ml | mcg/L  | Carr Units | Pg/ml        |

Markers of oxidative stress included IsoPs and DROMs. Concentration of DROMs was determined using spectrometry (505 nm) (8). IsoPs were quantified by gas chromatography/mass spectrometry using computer interference (9). Systemic inflammatory markers [hs-CRP, interleukin-6 (IL-6), interleukin 1β (IL-1β), and tumor necrosis factor-α (TNF-α)] were measured using commercially available assay kits.

Categorical variables were compared using Chi-square tests while continuous variables were compared using analyses of variance. Multiple logistic regression models were used to analyze independent associations of DROMs and hs-CRP with CHADS-2 risk categories. An interaction model was used to evaluate covariance between hs-CRP and DROMs in their association with CHADS-2 risk categories. A biomarker risk model was constructed giving a score of 1 for each abnormal DROMs or hs-CRP value, and this was correlated with CHADS-2 risk scores.

The results of the assays are shown in Table 1.

TABLE 1

|  | CHADS-2 Risk Categories | | | |
| --- | --- | --- | --- | --- |
| Variables | 0 (No risk) | 1 (Intermediate risk) | 2 (Severe risk) | P-value |
| Age (years) | 60.0 ± 7.4 | 57.6 ± 12.4 | 59.9 ± 17.0 | 0.8 |
| Males (%) | 90.0% | 91.7% | 65.0% | 0.04 |
| Whites (%) | 95.0% | 87.5% | 70% | 0.09 |
| BMI (kg/m$^2$) | 32.0 ± 9.1 | 34.4 ± 12.2 | 34.6 ± 14.8 | 0.8 |
| Smokers (%) | 30.0% | 20.8% | 10.0% | 0.3 |
| HTN (%) | 5.3% | 75.0% | 65.0% | <0.001 |
| Diabetes (%) | 5.0% | 4.3% | 20.0% | 0.1 |
| Coumadin (%) | 90.0% | 91.7% | 85.0% | 0.8 |

Figure 2:
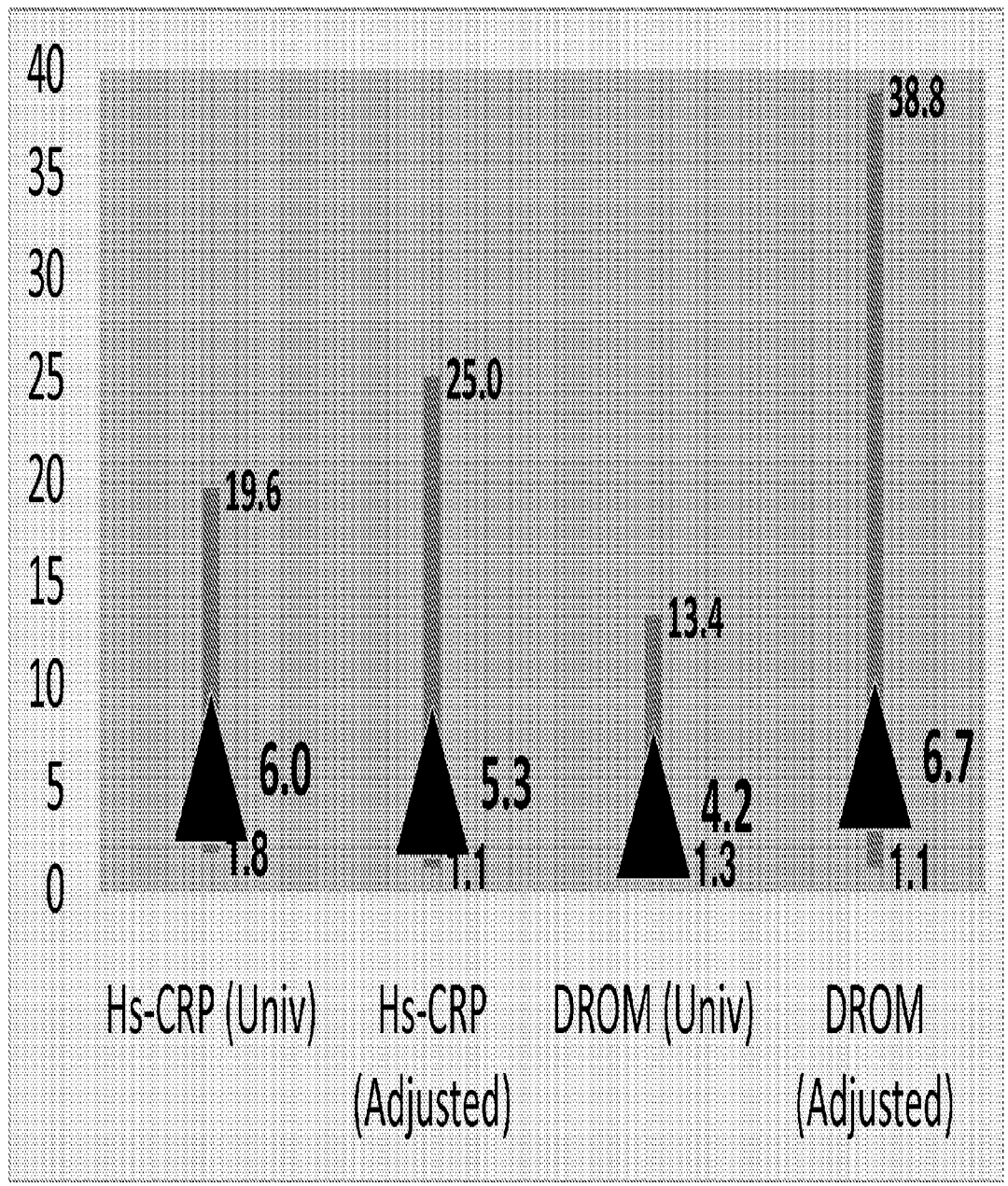
FIG. 2 is a graph representing the univariate and adjusted odds ratios of CRP and DROMs for intermediate to severe CHADS2 risk categories.

CHADS-2, C = congestive heart failure, H = hypertension, A - Age ≥75 years, D = presence of diabetes mellitus, S = history of stroke or transient ischemic attack;
BMI = body mass index;
HTN = hypertension Sixty-four subjects were enrolled in this study. Based on their CHADS-2 scores, 20 subjects were categorized as 0 (no-risk), 24 as 1 (intermediate-risk) and 20 as 2 (severe-risk). Subjects in the three risk categories were similar in mean age (p=0.83), smoking status (p=0.29) and diabetes (p=0.14), but differed in gender distribution (p=0.04) and hypertension (p<0.001). CHADS-2 risk categories significantly differed in having abnormal hs-CRP (0=40.0%, 1=70.0%, 2=90.0%; p=0.003) and DROMs (0=45%, 1=78.3%, 2=80%; p=0.04). No difference was found in IL-1β, IL-6, TNF-α and IsoPs. (FIG. 1) Subjects with intermediate to severe CHADS-2 risk retained significant association with abnormal hs-CRP (OR: 5.3, 95% CI: 1.1-25.0) and DROMs (adjusted OR: 6.7, 95% CI: 1.2-38.8) after adjusting for gender and hypertension. There was no significant interaction between hs-CRP and DROMs in their association with CHADS-2 risk categories in multiple logistic interaction model (p=0.64). (FIG. 2) A biomarker risk model, combining hs-CRP and DROMs, correlated well with the CHAD-2 risk categories (r=0.49, p<0.001).

Example 2

This example provides a method of calculating a CHADS2 and CHA$_2$DS$_2$-VASc score for stroke risk prediction.

Subjects, or the medical records thereof, are evaluated for the presence or history of the conditions listed in the CHADS2 table below. For each condition which is present in the subject or in the history of the subject, the number of points indicated in the right-most column of the table is added to the subject's score. The final CHADS2 score represents the sum of the points.

CHADS2

| | Condition | Points |
| --- | --- | --- |
| C | Congestive heart failure | 1 |
| H | Hypertension: blood pressure consistently above 140/90 mmHg (or treated hypertension on medication) | 1 |
| A | Age ≥75 years | 1 |
| D | Diabetes mellitus | 1 |
| S$_2$ | Prior Stroke or TIA | 2 |

Subjects, or the medical records thereof, are evaluated for the presence or history of the conditions listed in the CHA$_2$DS$_2$-VASc table below. For each condition which is present in the subject or in the history of the subject, the number of points indicated in the right-most column of the table is added to the subject's score. The final CHA$_2$DS$_2$-VASc score represents the sum of the points.

CHA$_2$DS$_2$-VASc

| | Condition | Points |
| --- | --- | --- |
| C | Congestive heart failure (or Left ventricular systolic dysfunction) | 1 |
| H | Hypertension: blood pressure consistently above 140/90 mmHg (or treated hypertension on medication) | 1 |
| A$_2$ | Age ≥75 years | 2 |
| D | Diabetes Mellitus | 1 |
| S$_2$ | Prior Stroke or TIA or thromboembolism | 2 |
| V | Vascular disease (eg. peripheral artery disease, myocardial infarction, aortic plaque) | 1 |
| A | Age 65-74 years | 1 |
| Sc | Sex category (i.e., female gender) | 1 |

Example 3

This example demonstrates a method of calculating a risk level of stroke, according to a method of the invention.

A level of DROMs is measured in a biological sample, e.g., blood, obtained from the subject. The measured level is compared to a control level, e.g., a level of a subject known to not have a risk for stroke (e.g., a subject that does not exhibit any one or more of atrial fibrillation, atrial flutter, diabetes, hypertension).

The medical records of the subject is evaluated and a stroke risk stratification scheme score is then determined, per one of the two tables below.

| Condition | Points |
| --- | --- |
| Congestive heart failure | 1 |
| Hypertension: blood pressure consistently above 140/90 mmHg (or treated hypertension on medication) | 1 |
| Age ≥75 years | 1 |
| Diabetes mellitus | 1 |
| Increased DROMs level | 1 |
| Prior Stroke or TIA | 2 |

| Condition | Points |
| --- | --- |
| Congestive heart failure | 1 |
| Increased CRP level | 1 |
| Hypertension: blood pressure consistently above 140/90 mmHg (or treated hypertension on medication) | 1 |
| Age ≥75 years | 1 |
| Diabetes mellitus | 1 |
| Increased DROMs level | 1 |
| Prior Stroke or TIA | 2 |

Optionally, the subject's need for anti-coagulation therapy is determined, according to the risk level stratification scheme, as outlined in either of the two tables below:

| CHADS2 score | DROMs level (relative to a control level) | DROMs/CHADS2 Risk Level of Stroke | Need for anti-coagulation therapy? |
| --- | --- | --- | --- |
| 0 | No increase | A | No |
| 0 | Increased | B | Yes |
| 1 | No increase | C | No |
| 1 | Increased | D | Yes |
| 2 | Increased | E | Yes |

-continued

| CHADS2 score | DROMs level (relative to a control level) | DROMs/CHADS2 Risk Level of Stroke | Need for anti-coagulation therapy? |
|---|---|---|---|
| 3 | Increased | F | Yes |
| 4 | Increased | G | Yes |
| 5 | Increased | H | Yes |
| 6 | Increased | I | Yes |

| CHADS2 score | CRP and/or DROMs level (relative to a control level) | DROMs/CRP/CHADS2 Risk Level of Stroke | Need for anti-coagulation therapy? |
|---|---|---|---|
| 0 | No increase | A | No |
| 0 | Increased | B | Yes |
| 1 | No increase | C | No |
| 1 | Increased | D | Yes |
| 2 | Increased | E | Yes |
| 3 | Increased | F | Yes |
| 4 | Increased | G | Yes |
| 5 | Increased | H | Yes |
| 6 | Increased | I | Yes |

REFERENCES

The following represents a reference list numbered according to the citation numbering used in Example 1:

1. Heart disease and stroke statistics—2011 update: a report from the American Heart Association. American Heart Association Statistics Committee and Stroke Statistics Subcommittee. Circulation. 2011 Feb. 1; 123(4):e18-e209.

2. Atrial Fibrillation Investigators. Risk factors for stroke and efficacy of antithrombotic therapy in atrial fibrillation: analysis of pooled data from five randomized controlled trials. Arch Intern Med 1994; 154:1449-57.

3. Gage B F, Waterman A D, Shannon W, Boechler M, Rich M W, Radford M J. Validation of clinical classification schemes for predicting stroke: results from the National Registry of Atrial Fibrillation. JAMA. 2001 Jun. 13; 285(22): 2864-70.

4. Wang T J, Massaro J M, Levy D, Vasan R S, Wolf P A, D'Agostino R B et al. A risk score for predicting stroke or death in individuals with new-onset atrial fibrillation in the community: the Framingham Heart Study. JAMA. 2003 Aug. 27; 290(8):1049-56.

5. Chung M K, Martin D O, Sprecher D, Wazni O, Kanderian A, Carnes C A et al. C reactive protein elevation in patients with atrial arrhythmias: inflammatory mechanisms and persistence of atrial fibrillation. Circulation 2001; 104: 2886-91.

6. Conway D S, Buggins P, Hughes E, Lip G Y. Predictive values of indices of inflammation and hypercoaguability on success of cardioversion in persistent atrial fibrillation. Am J Cardiol 2004; 94: 508-10.

7. Neuman R B, Bloom H L, Shukrullah I, Darrow L A, Kleinbaum D, Jones D P, Dudley S C Jr. Oxidative stress markers are associated with persistent atrial fibrillation. Clin. Chem., 2007, 53, 1652-7.

8. Cornelli U, Terranova R, Luca S, Cornelli M, Alberti A: Bioavailability and antioxidant activity of some food supplements in men and women using the DROM tests as a marker of oxidative stress. J Nutr 131; 3208-3211.

9. Roberts L J, Milne G L: Isoprostanes. J Lipid Res 2009; 50:S219-S223.

10. Crandall M A, Home B D, Day J D, Anderson J L, Muhlestein J B, Crandall B G et al. Atrial fibrillation and CHADS2 risk factors are associated with highly sensitive C-reactive protein incrementally and independently. Pacing Clin Electrophysiol. 2009 May; 32(5):648-52.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein are performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed:

1. A method of determining a subject's need for anti-coagulation therapy, wherein the subject exhibits atrial fibrillation or atrial flutter and has a CHADS2 or CHA$_2$DS$_2$-VASc score which is less than 2, comprising the steps of (i) measuring a level of derivatives of reactive oxygen metabolites (DROMs) in a biological sample obtained from the subject, and (ii) when the level of DROMs is increased, relative to a control level, determining the subject as a subject in need for anti-coagulation therapy.

2. The method of claim 1, further comprising the step of administering to the subject an anti-coagulant in a therapeutically effective amount.

3. The method of claim 1, wherein the subject has a CHADS2 or CHA$_2$DS$_2$-VASc score of 1 or 0.

4. The method of claim 1, further comprising the step of measuring a level of C-reactive protein (hs-CRP), in a biological sample obtained from the subject.

5. The method of claim 1, further comprising the step of evaluating the subject's medical record for increased levels of hsCRP.

6. A method of determining a subject's need for anti-coagulation therapy, comprising the steps of (i) measuring a level of derivatives of reactive oxygen metabolites (DROMs) in a biological sample obtained from the subject, (ii) measuring a level of C-reactive protein (hs-CRP), in a biological sample obtained from the subject or evaluating the subject's medical record for increased levels of hsCRP, and (iii) determining the subject as a subject in need for anti-coagulation therapy, when the level of DROMs and the level of hs-CRP, relative to a control level, is increased.

* * * * *

SEQUENCE LISTING

<160> NUMBER OF SEQ ID NOS: 2

<210> SEQ ID NO 1
<211> LENGTH: 224

<212> TYPE: PRT
<213> ORGANISM: Homo sapiens

<400> SEQUENCE: 1

```
Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr
50                  55                  60

Arg Gly Tyr Ser Ile Phe Ser Tyr Ala Thr Lys Arg Gln Asp Asn Glu
65                  70                  75                  80

Ile Leu Ile Phe Trp Ser Lys Asp Ile Gly Tyr Ser Phe Thr Val Gly
                85                  90                  95

Gly Ser Glu Ile Leu Phe Glu Val Pro Glu Val Thr Val Ala Pro Val
            100                 105                 110

His Ile Cys Thr Ser Trp Glu Ser Ala Ser Gly Ile Val Glu Phe Trp
        115                 120                 125

Val Asp Gly Lys Pro Arg Val Arg Lys Ser Leu Lys Lys Gly Tyr Thr
130                 135                 140

Val Gly Ala Glu Ala Ser Ile Ile Leu Gly Gln Glu Gln Asp Ser Phe
145                 150                 155                 160

Gly Gly Asn Phe Glu Gly Ser Gln Ser Leu Val Gly Asp Ile Gly Asn
                165                 170                 175

Val Asn Met Trp Asp Phe Val Leu Ser Pro Asp Glu Ile Asn Thr Ile
            180                 185                 190

Tyr Leu Gly Gly Pro Phe Ser Pro Asn Val Leu Asn Trp Arg Ala Leu
        195                 200                 205

Lys Tyr Glu Val Gln Gly Glu Val Phe Thr Lys Pro Gln Leu Trp Pro
210                 215                 220
```

<210> SEQ ID NO 2
<211> LENGTH: 206
<212> TYPE: PRT
<213> ORGANISM: Homo sapiens

<400> SEQUENCE: 2

```
Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
            100                 105                 110

Gly Lys Pro Arg Val Arg Lys Ser Leu Lys Lys Gly Tyr Thr Val Gly
        115                 120                 125

Ala Glu Ala Ser Ile Ile Leu Gly Gln Glu Gln Asp Ser Phe Gly Gly
```

-continued

```
                130                 135                 140
Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
                180                 185                 190

Glu Val Gln Gly Glu Val Phe Thr Lys Pro Gln Leu Trp Pro
                195                 200                 205
```